United States Patent [19]

Pincus

[11] Patent Number: 4,874,695
[45] Date of Patent: Oct. 17, 1989

[54] RAPID INDENTIFICATION OF YEAST AND OTHER FUNGAL MICROORGANISMS BY ENZYME DETECTION

[75] Inventor: David H. Pincus, New Hyde Park, N.Y.

[73] Assignee: American Home Products Corp., New York, N.Y.

[21] Appl. No.: 703,644

[22] Filed: Feb. 21, 1985

Related U.S. Application Data

[63] Continuation-in-part of Ser. No. 473,381, Mar. 8, 1983, abandoned.

[51] Int. Cl.$^4$ .......................... C12Q 1/44; C12Q 1/36; C12Q 1/04; C12P 19/24
[52] U.S. Cl. ........................................ 435/19; 435/24; 435/34; 435/94; 435/254; 435/255; 435/256; 435/257; 435/810; 435/922; 435/924; 435/930; 435/942; 435/944; 435/946
[58] Field of Search ................... 435/24, 34, 254, 255, 435/256, 921, 922, 924, 930, 942, 944, 257, 946, 911, 19, 81

[56] References Cited

U.S. PATENT DOCUMENTS

| | | | |
|---|---|---|---|
| 4,030,980 | 6/1977 | Beckford et al. | 435/942 |
| 4,308,348 | 12/1981 | Monget | 435/873 |
| 4,591,554 | 5/1986 | Koumura et al. | 435/34 X |
| 4,603,108 | 7/1986 | Bascomb | 435/34 |
| 4,728,607 | 3/1988 | Dorn et al. | 435/34 |

FOREIGN PATENT DOCUMENTS

| | | | |
|---|---|---|---|
| 2031949 | 4/1980 | United Kingdom . | |
| 8002295 | 10/1980 | World Int. Prop. O. | 435/34 |

OTHER PUBLICATIONS

Barry, Arthur, Clinics in Laboratory Medicine, vol. 5, No. 1, Mar. 1985, p. 3, H, 16, Biological Review 26:24615.
Jones et al., Journal of General Microbiology, (1982), 1101–1107.
Silva–Hunter et al., in Manual of Clinical Microbiology, 2nd edition, 1974, pp. 491–507.
Barman, Enzyme Handbook, vol. II, Springer-Verlag, New York Inc., 1969, p. 602.
Bobey et al., Poster Secession Annual Meeting of The American Society for Microbiology, 1980.
Watson, (1976), Methods in Microbiology, vol. 9, pp. 1–14.
McGinnis, M. R., Lab. Hbk. of Med. Mycology, 1980, pp. 264, 337, 341, 346, 395, 611.
Ainsworth, G. C., Ainsworth & Bisby's Dictionary of the Fungi, 6th Ed., (1971), p. 626.
Lee & Febiger, Medical Mycology, 3rd Ed., (1977), pp. 185, 203, 515, 529.
Davenport, R. R., "An Introduction to Yeasts and Yeast Like Organisms", pp. 1–27, from The Society for Applied Bacteriology Symposium, Series No. 9, titled Biology and Activity of Yeasts, Ed'd by F. A. Skinner et al., (1980).
Casal Roman et al., J. Clin. Microb., vol. 18, No. 12, Aug. 1983.
Lee et al., Sabouraudia, (1975), vol. 13, Part 2, pp. 132–141.
Bobey et al., Abstracts of the Annual Mtg. ASM, USA, May 11–16, 1980, p. 317 (C254).
Bobey et al., J. Clin. Microb., vol. 13, No. 2, Feb. 1981, pp. 393–394.
M'n'l. Clin. Microb., Chps. 52 & 55, 3rd Ed., Lennette et al.

Primary Examiner—Robert J. Warden
Assistant Examiner—Carol A. Spiegel
Attorney, Agent, or Firm—Adley F. Mandel

[57] ABSTRACT

Rapid identification of different species of microorganism selected from fungi and yeast like algae is accomplished by culturing the microorganism for several hours under normal conditions on a non-inhibitory mycological medium which stimulates the microorganism to make characteristic enzymes by which the microorganism can be identified, distributing the culture (in suspension) onto several supports containing different substrates which are capable of reacting with the enzymes so produced by the different species of microorganisms; and rapidly incubating the admixture to produce a distinctly colored or colorable reaction product.

13 Claims, No Drawings

RAPID INDENTIFICATION OF YEAST AND OTHER FUNGAL MICROORGANISMS BY ENZYME DETECTION

This is a continuation-in-part of application Ser. No. 473,381, filed Mar. 8, 1983, now abandoned.

BACKGROUND OF THE INVENTION

An increase in the incidence of infections caused by various fungi, e.g., yeasts, and yeast like algae in recent years has emphasized the need for a rapid means of their identification. In a compromised individual a yeast infection often proves rapidly fatal. Thus, providing the physician with an accurate, same-day (rapid) identification can influence a more effective treatment for the infected patient.

Fungi are ubiquitous, eucaryotic microorganisms and differ in many ways from bacteria. Yeasts for example, grow more slowly than bacteria—a mature culture requires 48-72 hours incubation in contrast to 18-24 hours for most bacteria.

Current identification procedures for fungi and yeast like organisms also require more time for incubation (with test substrates) than those used for bacteria. Thus, the two most frequently used commercial systems for identification of yeasts require incubation times after primary plate isolation of 3 and 6 days. Most commercial systems are modifications of either or both of two conventional techniques: Auxanographic or Wickerham procedures. The Wickerham procedure represents the classical, traditional approach to yeast taxonomy, but due to the tedious nature of this method (i.e., extensive media preparation, pipetting into multiple racks of test tubes and incubation for up to 6 weeks) mycologists have widely accepted more rapid modifications affording a high degree of reliability. The more rapid conventionally accepted method is Auxanography which examines the patterns produced by various carbohydrates supporting growth in the presence of a growth medium. Both the Wickerham and auxanographic methods utilize carbohydrates by assimilation in the presence of what is commonly known as Wickerham's yeast nitrogen base.

Carbohydrate fermentation tests have also been employed for the detection of yeasts. However these tests are more subject to variation than assimilations and are only considered reliable for yeasts when the fermentation process produces detectable gas. As with the assimilations, carbohydrate fermentation tests for yeasts rely on the further employment of a basal (growth) medium.

While both assimilation and fermentation carbohydrate tests have in isolated cases been rapidized to some degree, the most reliable identifications are attained only through longer incubation periods with the test substrates—for days or weeks.

More recently, the API ZYM System (Analytab Products, Plainview, New York) a system designed for the detection of enzyme activities with certain chromogenic substrates has been assessed as a means for generating enzymatic profiles which might be useful for the rapid identification of medically significant yeasts. (Bobey et al. ASM Ann'l. Mtg. 1980, Poster #C-254). The authors of that study considered that the ZYM system had the potential to distinguish between various yeasts, but too few isolates had been examined to determine whether characteristic patterns would emerge enabling identification.

Bobey and Ederer also investigated the use of fluorogenic substrates to access their usefulness in the rapid identification of medically significant yeast isolates (J. Clin. Micro., Feb., 1981, p. 393-394, Vol. 13, No. 2).

Currently there is no available system which applies or is capable of applying the technology of chromogenic substrates to the identification of yeasts and yeast like organisms.

Collection, transport and isolation of specimens relating to fungi are further explained, for example, in Chapters 52 and 55 of the 3rd Edition of the Manual of Clinical Microbiology (1980), both said chapters are herein expressly incorporated by reference. Another reference may be found in The Yeasts, 1970, 2nd Edition by J. Lodder.

SUMMARY OF THE INVENTION

This invention relates to a method for the rapid identification of microorganisms selected from the group consisting of fungi and yeast like algae and genera and species thereof. More particularly the method of the invention enables the rapid identification of the aforementioned microorganisms, through a colorimetric detection of characteristic enzymes via a selected battery of chromogenic test substrates. The characteristic enzymes utilized herein are produced (or constituted) by the fungi or yeast like algae during growth on a mycological culture medium.

In another embodiment the present invention relates to a fungi or yeast like algae test kit or device which provides a series of test chambers, preferably miniaturized test chambers, wherein each said test chamber contains one or more of a specified group of dried substrates sensitive to the enzymes characteristic of the subject microorganisms.

DETAILED DESCRIPTION OF THE INVENTION

Media used in the collection and isolation of fungal (e.g. yeast) cultures are not the same as those commonly employed in bacteriology. For example, while trypticase soy agar with 5% sheep blood is a very common isolation medium used for bacteria, Sabouraud dextrose agar (SDA) serves the analogous purpose in the mycological laboratory for the fungi. Other common media utilized in the mycology laboratory include potato dextrose agar, corn meal (with or without Tween ® 80, a polyoxyethylene (20) sorbitan monooleate) agar, and brain heart infusion (with or without blood) agar. Another useful tool to prevent overgrowth by bacteria or saprophytic fungi is an inhibitory medium such as Mycosel or Mycobiotic agar, both primarily used for isolation from direct clinical specimens.

In accordance with the invention, a method for the rapid identification of microorganisms selected from the group consisting of fungi, yeast like algae, and genera and species thereof is disclosed. The method is particularly applicable to yeasts and yeast like organisms.

The method first requires culturing of an unknown fungal or yeast like algal microorganisms in a mycological culture medium sufficiently to stimulate the production or multiply the presence of one or more enzymes characteristic of said microorganisms.

Following culturing of the unknown fungus or yeast like alga, a sufficient number of morphologically similar colonies of the microorganism containing said enzyme(s) are suspended and homogeneously mixed in an aqueous suspending medium to prepare an inoculum of the unknown microorganism.

The inoculum is then mixed with one or more substrates selected from a group consisting of primarily chromogenic substrates specific for said enzymes. These chromogenic substrates are capable of reacting with said enzyme(s) to produce a distinctively colored product or a product easily convertible to a distinctively colored product.

Finally, the admixture of the inoculum (yeast or yeast like suspension) with the substrate is incubated to obtain the product(s) whereby the unknown fungal or yeast like organism is identified by colorimetric display.

The chromogenic substrates of the invention for detecting the characteristic aminopeptidase enzymes produced in the method of the invention are derivatives of the amino acids specific to those enzymes with a product such as β-naphthylamine, p-nitroaniline and the like which provide β-naphthylamide, p-nitroanilide and the like substrates, whereby upon hydrolysis in the presence of said characteristic enzyme(s) a colored product, such as p-nitroaniline or a product easily convertible to a colored product (if not formulated to release a colored product) such as β-naphthylamine is produced. Thus a β-naphthylamine product will easily convert to a colored product in the presence of, for example, a diazo dye (a diazonium salt) selected from Fast Blue FF, Fast Blue B, Fast BR, Fast Violet B, and the like or in the presence of a cinnamldehyde reagent.

Similarly the chromogenic substrates for detecting the characteristic glycosidase, phosphatase, esterase and galactosaminidase enzymes produced in the method of the invention are derivatives of the various glycosides, phosphate, ester and galactosaminide with a product such as indoxyl, o-nitrophenol, p-nitrophenol, beta- or 2-naphthol, substituted naphthols and the like which provide indoxyl acetate, o-nitrophenyl- βD-xyloside, p-nitrophenyl-N-acetyl -βD-galactosaminide and the like substrates, whereby upon hydrolysis in the presence of said characteristic enzyme(s), a colored product such as indoxyl or a product easily convertible to a colored product (if not formulated to release a colored product) such as beta naphthol is produced. Thus a beta naphthol product will easily convert to a colored product in the presence of, for example, a diazo dye or a cinnamaldehyde reagent as above described.

The method and test kit of the invention have been successfully employed to identify and distinguish among the genera and species included in the genera of Aureobasidium, Blastoschizomyces, Candida, Cryptococcus, Geotrichum, Hanseniaspora, Hansenula, Kluyveromyces, Pichia, Prototheca, Rhodotorula, Saccharomyces, Sporobolomyces, Torulaspora, Torulopsis and Trichosporon. By means of this invention, many of the more difficult separable pairs of species of fungi and yeast like algae because of common characteristics are now easily separated and identified.

The presence or absence of the characteristic eznymes produced or multiplied from fungal or yeast like algal microorganisms is detected via a first group of substrates capable of detecting an enzyme selected from the group consisting of acetate esterase, leucyl-glycine aminopeptidase and glycyl-glycine aminopeptidase. For this purpose the preferred group of substrates are respectively indoxyl acetate, leucyl-glycine-β-naphthylamide and glycyl-glycine-β-naphthylamide. This first group of substrates may be further augmented to include p-nitrophenyl-N-acetyl-βD-galactosaminide to detect the enzyme, N-acetyl-βD-galactosaminidase and L-proline-p-nitroanilide to detect the enzyme L-proline aminopeptidase.

The method and test kit of the invention are made more desirable and useful by including other groups of substrates for detecting the presence or absence of other enzymes including most of a second group of substrates selected from a second group consisting of p-nitrophenyl phosphate, p-nitrophenyl-βD-fucoside, p-nitrophenyl-αD-glucoside, p-nitrophenyl-βD-glucoside, and o-nitrophenyl-βD-xyloside.

In a preferred embodiment the method and test kit of the invention will include most of a third group of substrates selected from a third group consisting of the β-naphthylamides of glycine, L-proline, L-tryptophan, L-hydroxyproline, L-isoleucine, L-valine, L-histidine, L-tyrosine and the di- β-naphthylamide of L-cystine.

Selection of most of the substrates as described from the three groups together with a urea substrate for detecting urease provide a battery of tests for identifying substantially all of the clinically significant fungal and yeast like algae through detection of some of their characteristic enzymes.

Table I herein lists substrates selected from the disclosed groups of substrates to provide a preferred battery of tests for identifying fungi and yeast like algae.

TABLE I

| | Test Substrate |
|---|---|
| 1. | urea |
| 2. | p-nitrophenyl(pnp)-phosphate |
| 3. | pnp-βD-fucoside |
| 4. | pnp-βD-glucoside |
| 5. | pnp-N-acetyl-βD-galactosaminide |
| 6. | pnp-αD-glucoside |
| 7. | o-nitrophenyl-βD-xyloside |
| 8. | L-proline-p-nitroanilide |
| 9. | indoxylacetate |
| 10. | glycine-β-naphthylamide (BNA) |
| 11. | L-proline-BNA |
| 12. | L-tryptophan(e)-BNA |
| 13. | L-hydroxyproline-BNA |
| 14. | L-isoleucine-BNA |
| 15. | L-valine-BNA |
| 16. | L-leucyl-glycine-BNA |
| 17. | L-histidine-BNA |
| 18. | L-cystine-di-BNA |
| 19. | L-tyrosine-BNA |
| 20. | glycyl-glycine-BNA |

The availablility of measurable, multiple distinguishing characteristics improve the reliability of the identification of both typical and atypical organisms as they are encountered.

Table II herein lists some of the more difficult (biochemically) separable pairs (including those previously listed) of microorganisms encountered in clincial practice and lists some of the test substrates by numerical refrence to Table I which normally distinguish and identify each of the species in the listed pair.

TABLE II

| Species Pair | | Normally Distinguishing Test |
|---|---|---|
| B.(Tr.) capitatum vs. | C. krusei | 11,14,20 |
| | C. lambica | 9,20 |
| | C. lipolytica | 8,13,14,15 |
| | Pr. stagnora | 8,9,11,12,14,15,17 |
| | Pr. zopfii | 9,12,13,14,15,16,17 |
| | T. glabrata | 9,11 |
| C. albicans vs. | C. lusitaniae | 4,5,6,9,15 |
| | C. parapsilosis | 5,9,10,14,15 |
| | C. paratropicalis | 4,5,6,8,9,10,11,13,15, 16,20 |

TABLE II-continued

| Species Pair | | Normally Distinguishing Test |
|---|---|---|
| | C. stellatoidea | 8,9,13,15,20 |
| | C. tropicalis | 4,5,6,8,9,10,11,13,15, 16,20 |
| C. guilliermondii vs. | T. candida | 6,12,17,20 |
| C. krusei vs. | C. lambica | 9 |
| | C. lipolytica | 8,11,13,15,20 |
| | Pr. zopfii | 9,11,12,13,15,17 |
| | T. glabrata | 9,14,20 |
| C. lambica vs. | C. lipolytica | 15,20 |
| | Pr. zopfii | 12,15,16,17 |
| | T. glabrata | 20 |
| C. lipolytica vs. | Pr. zopfii | 16,17 |
| | T. glabrata | 8,11,13,14,15 |
| C. lusitaniae vs. | C. parapsilosis | 14 |
| | C. tropicalis | 8,11,13,16 |
| | T. candida | 6,9,12,17 |
| C. parapsilosis vs. | C. tropicalis | 8,11,13,14,16 |
| C. paratropicalis vs. | C. stellatoidea | 5,6,16 |
| C. rugosa vs. | Geotrichum sp. | 2,5,8,11,13,15,16 |
| C. stellatoidea vs. | Cr. terreus | 1,5,8,9,13,14 |
| Cr. albidus vs. | Cr. laurentii | 8,10,11,12,13,15,16, 17,19 |
| | Cr. neoformans | 6,7,8,9,10,11,12,13, 15,16,17,19 |
| | Cr. uniguttulatus | 6,7,9,14 |
| | Tr. beigelii | 12,15,19 |
| Cr. laurentii vs. | Tr. beigelii | 11,13,16,17 |
| Cr. neoformans vs. | Cr. uniguttulatus | 8,11,12,13,14,15,16 |
| | Tr. beigelii | 6,9,11,13,16,17 |
| Hs. guilliermondii vs. | Hs. uvarum | |
| H. anomala vs. | Rh. glutinis | 1,7,8,13 |
| | Rh. rubra | 1,7,8,13,18 |
| | S. cerevisiae | 4,6,7,9,14,18,19 |
| Pr. stagnora vs. | S. cerevisiae | 8,12,15,17 |
| Pr. wickerhamii vs. | T. glabrata | 8,11,12,13,14,15,17 |
| Rh. glutinis vs. | Rh. rubra | 18 |
| | S. cerevisiae | 1,4,8,9,11,13,14,18,19 |
| Rh. pilimanae vs. | Sp. salmonicolor | |
| Rh. rubra vs. | S. cerevisiae | 1,4,8,9,11,13,14,19 |
| S. cerevisiae vs. | Sp. salmonicolor | 1,8,9,11,13,14,19 |
| T. candida vs. | Tr. beigelii | 1,6,9,16,17 |

In fact of the 946 pair possibilities in 43 different species already evaluated by the method and device of the invention, less than 1.16% provided any difficulty with respect to pair separation and these were all generally identified and separated including the atypical specie variations therefor by means of the differential values provided by the battery of tests.

Viewed differently, Table III lists some of the organisms studies with the method and device of the invention and some of the distinguishing groups of tests as provided with one possible scheme of analysis with numerical reference to the test substrates in Table I which are normally sufficient to identify that organism or a pair of organisms.

TABLE III

| ORGANISM | Schemes |
|---|---|
| A. Aureobasidium pullulans | 1,4,9,15–17,19 |
| B. Blastoschizomyces (Tr.) Capitatum | 1,4,9,11,15,16 |
| C. Candida albicans | 4,8,9,12,16 |
| D. C. ciferrii | 1,3,5,8,12,16 |
| E. C. guilliermondii | 4,8,9,12,16 or 5,8,9,14, 16,17 |
| F. C. intermedia | 4,8,9,16,17 |
| G. C. krusei | 3–5,8,12,16 or 1,4,9,11, 15,16 |
| H. C. lambica | 1,3,9,11,15,16,20 or 1,9, 11,15,16,20 |
| I. C. lipolytica | 1,6,11,15–17 |
| J. C. lusitaniae | 5,8,9,14,16,17 |
| K. C. parapsilosis | 5,8,9,14,16,17 |
| L. C. paratropicalis | 1,4,7,9,15,16 |
| M. C. pseudotropicalis | 2,3,8,16 or 1,3,9,11,15,16 |
| N. C. rugosa | 5,8,9,16,17 |
| O. C. stellatoidea | 3,5,8,12,16 |
| P. C. tropicalis | 1,4,7,9,15,16 |
| Q. C. zeylanoides | 4,8,9,16,17 |
| R. Cryptococcus albidus | 1,4,7,16,19 |
| S. Cr. laurentii | 1,3,8,12,16 |
| T. Cr. neoformans | 1,3,8,12,16 |
| U. Cr. terreus | 4,8,9,12,16 |
| V. Cr. uniguttulatus | 1,4,7,9,16,19 or 1,4,9,16, 19 |
| W. Geotrichum sp. | 1,2,11,15,16 |
| X. Hanseniaspora guilliermondii | 2,3,8,16 |
| Y. Hs. uvarum | 2,3,8,16 |
| Z. Hs. valbyensis | 2,3,8,16 |
| AA. Hansenula anomala | 1,4,7,9,15,16 |
| BB. Kluyveromyces lactis | 3–5,8,12,16 |
| CC. K. vanudenii | 1,3,9,11,15,16,20 |
| DD. Prototheca stagnora | 1,2,11,15,16 or 8,9,11,12, 16,20 |
| EE. Pr. wickerhamii | 1,6,11,15–17 |
| FF. Pr. zopfii | 1,3,5,8,12,16 or 8,9,11,12, 16 |
| GG. Rhodotorula glutinis | 1,4,7,9,16,18,19 |
| HH. Rh. minuta | 1,4,9,15–17,19 |
| II. Rh. pilimanae | 1,4,6,16 |
| JJ. Rh. rubra | 1,4,7,9,16,18,19 |
| KK. Saccharomyces cerevisiae | 1,9,11,14–16,20 |
| LL. Sporobolomyces salmonicolor | 1,4,6,16 |
| MM. Torulaspora rosei | 1,3,9,11,15,16,20 |
| NN. Torulopsis candida | 1,3,5,8,12,16 or 8,9,11,12, 16,20 |
| OO. T. glabrata | 1,9,11,14–16,20 |
| PP. Trichosporon beigellii | 1,4,6,16, or 1,4,9,15,16,19 |
| QQ. Pichia Ohmeri | 1,6,11,15,16 |

It will be readily apparent to one skilled in the art that by means of the above described scheme of analysis or different schemes involving different sets of substrates and other distinguishing tests provided by the method and device or test kit of the invention, that reliably accurate results identifying various fungi and yeast like algae are readily obtainable.

Table IV herein lists some of the other organisms detected by other test substrates through the enzymes normally produced by incubation of said organisms on an SDA plate such that an aqueous suspension of colonies of the incubated organism causes hydrolysis of a test substrate molecule to release a colored product or a products easily converted to a colored product said products selected from the group consisting of o-nitrophenol, p-nitrophenol, p-nitroaniline, β-naphthol, β-naphthylamine, 4-methoxy-β-naphthylamine, 6-bromo-2-naphthol, 1-naphthol, Naphthol AS, Indoxyl and the like. The numbering in Table IV follows the numbering of Table I and the lettering of Table III, and "AP" represents aminopeptidase.

TABLE IV

| Test Substrate | Detected Enzyme | Organism Normally Detected | Organism Normally Not Detected |
|---|---|---|---|
| 1 | urease | A,R-V,GG-JJ,LL,PP | B-Q,W-FF,QQ,KK,MM-OO |
| 2 | phosphatase | A,B,D-V,AA-GG,II, JJ,LL-PP | W-Z |
| 3 | βD-fucosidase | M,X-Z | A-L,N-W,BB-GG,QQ,II-OO |

TABLE IV-continued

| Test Substrate | Detected Enzyme | Organism Normally Detected | Organism Normally Not Detected |
|---|---|---|---|
| 4 | βD-glucosidase | A,D-F,J,L-M,P,R,S,U,V,X-DD,QQ,GG,HH,JJ | B-C,G-H,N,Q,DD-FF,KK-MM,OO,II |
| 5 | N—acetyl-βD galactosaminidase | C,D,N,O | A,B,E-M,P-QQ |
| 6 | αD-glucosidase | E,F,J,L,P,AA,BB,QQ,PP | A-D,G-I,M-O,Q,T,V-Z CC-FF,II,KK-OO |
| 7 | βD-xylosidase | R,X-AA | B,C,E,G-I,K-Q,T-W,BB-OO,QQ |
| 8 | L-proline AP (pna) | C,E,F,I-K,N,Q,R U,V,QQ,DD,EE,GG-JJ,LL | B,D,G,L,M,O,P,S,T,W-CC, KK,MM,OO |
| 9 | acetate esterase | A,B,F,G,J-L,N-R,AA,QQ GG-JJ,LL,PP | C,D,H,M,T-V,X-Z,BB, CC,DD-FF,KK,MM-OO |
| 10 | glycine AP | A,B,E-I,K-N,P,R,U, W,AA-EE,GG-OO,QQ | C,Q,S,T,X,Y,Z |
| 11 | L-proline AP (BNA) | A-C,E,F,I-K,M,N,Q,R, U,V,X,Y,CC,EE-JJ,LL, MM,PP,QQ | D,G,L,P,S,T,W,DD,KK,OO |
| 12 | L-tryptophan(e) AP | B,C,E-H,J,L,M,O,P,R,U-Y AA-CC,QQ,GG,II-MM,OO | D,Q,S,T,DD-FF,NN,PP |
| 13 | L-hydroxyproline AP | C,E,F,I-K,N,Q,R,U,V,QQ, EE-JJ,LL,PP | B,D,G,L,M,O,P,S,T,W-CC KK,MM,OO |
| 14 | L-isoleucine AP | B,K,M,U,V,X,Y,AA CC,GG-JJ,LL,MM,OO | C,D,F,G,I,J,L,O-T KK,NN,PP |
| 15 | L-valine AP | A,B,E,G,H,J-P,R,U,V, X-CC,GG-MM,OO | C,D,I,Q,S,T,W,DD-FF QQ,PP |
| 16 | L-leucyl-glycine AP | A,B,H,I,L,P,R,V,W,AA, CC,EE,GG-MM,OO-QQ | C-F,J,K,N,O,Q,S-U,X-Z, BB,FF,NN |
| 17 | L-histidine AP | B,D,E,G-L,N-P,R,U,W,X, AA,CC,GG-MM,OO,PP | A,F,Q,S,T,BB,QQ,DD-FF,NN |
| 18 | L-cystine AP(di) | AA,CC,GG,MM | A-G,I-L,N-Z,BB,QQ,DD-FF, HH-LL,NN,PP |
| 19 | L-tyrosine AP | R,AA,GG,JJ,LL | A-L,N-Q,S-U,W-Z,BB-FF, HH,KK,NN-QQ |
| 20 | glycyl-glycine AP | A,B,E,I,L-P,W,AA-EE, QQ,HH,JJ-MM,OO | C,D,F-H,Q,S,T,X-Z,NN,PP |

According to the present invention, colorimetric detection of the characteristic enzymes herein disclosed, taken together or separately, is performed after putting a substrate into contact with a suspended culture of a fungus or yeast like microorganism grown on a medium, the composition of which stimulates or induces the production by said microorganism, of the earlier noted characteristic enzymes. The influence of the culture medium is therefore important, because the ability of the fungue or yeast like organism to produce the above characteristic enzymes is dependent on the medium on which the test microorganism is grown.

It has been found that production of the characteristic enzymes of the fungi and yeast like algae according to this invention, is optimal when the culture medium, from whence the colony used in the inoculum is taken, is a non-inhibitory medium (including brain heart infusion agar) and preferably SDA. A typical composition for SDA includes: Dextrose-40g; Neopeptone or Polypeptone-10 g or a combination of Pancreatic digest of casein USP-(5G) and Peptic digest of animal tissue USP-(5 g); Agar-20 or 15 g; Deminieralized Water-1 liter; final pH 5.6. These ingredients are heated to complete dissolution, dispensed in tubes (18-25mm in diameter) and autoclaved at 121° C. for 10 minutes or first autoclaved and then filled into appropriate sized petri dishes (e.g. 100 mm).

In addition it is advantageous in carrying out the various tests to formulate into the substrate a buffer to maintain the pH. Accordingly the substrate is normally prepared in a solvent such as water, dimethylformamide (DMF), methanol, acetone, dilute HCl or the like together with a buffer such as Tris-HCl, Tris, Trismaleate, monopotassium phohsate, disodium phosphate, dipotassium phosphate, Trizma base, N-tri-(hydroxymethyl)-methyl-3-amino-propane sulfonate, N-2-hydroxyethyl-piperazine-N'2-ethane sulfonate, N-2-hydroxy-ethylpiperazine-N'-3-propane sulfonate, N-tri(hydroxymethyl)-methyl-2-aminoethane sulfonic acid (TES), cyclohexylaminoethane sulfonic acid, sodium carbonate, potasssium carbonate, sodium borate and potassium borate.

In practice, applicants have employed solutions containing 4% w/v of the substrate numbered in Table I as 1; 0.275% of substrate 9; 0.2% of the substrates2-7; 0.1% of the substrates 8,15,19 and 20; 0.05% of the substrates 13,14 and 16-18; 0.03% of substrate 12; 0.025% of substrate 11; and 0.0125% of substrate 10. Substrates 1,3,4 and 6-9 were formulated with phosphate buffer; substrates 2 and 5 were formulated with TES buffer (N-tris[hydroxy-methyl]-methyl-2-aminoethanesulfonic acid); and substrates 10-20 were formulated with Tris buffer.

Additionally the solvent for substrate 1 was water with phosphate buffer to pH 6.5; for substrate 2, water with TES buffer to pH 7; for 3,4 and 6-8, 10% DMF with phosphate buffer to pH 8; for 5, 10% DMF with TES buffer to pH 8; for 9, 1.2% acetone with phosphate buffer to pH 7.6; for 10-20 respectively, 5,5,10,10,10,20,30,35,40,40 and 40 percent of DMF with Tris buffer to pH 8.

Forty microliters of each of the substrate solutions were filled into each reaction chamber of the device of the invention and dried.

Thus, in the present invention, the fungus or yeast like alga is cultured on an SDA plate for about 48-72 hours at 25°-30° C. The cultured fungal or algal specimen containing the induced or stimulated enzyme(s) is removed from the plate, as by a wooden applicator stick, inoculating loop or cotton swab, and suspended in (sterile) distilled water or saline, preferably water, in sufficient quantity so that the final turbidity is equivalent to that of at least a No. 3-4 McFarland (BaSO4) turbidity standard and preferably a No. 5 McFarland.

A test device containing one or more of the disclosed substrates in a series of reaction chambers is then inoculated (about 80-100 μl each) with the mycological suspension described above. These suspensions should be freshly used.

The inoculated reaction chambers on a strip plate should then be covered and rapidly incubated for about 2-6 hours, preferably 4 hours at about 36° C. in a non-$CO_2$ incubator and preferably in a humidified atmosphere. Reactions not requiring the addition of reagent may be read upon removal of the test device from the incubator, e.g., tests 1-9 in Table I. The remaining tests in Table I may all be read after the addition of 1 drop of cinnamaldehyde reagent and color development for 3 minutes. The color observed in each of the reaction chambers is then used to classify the fungus or yeast like algae as one of the species or groups for which the color is determinative.

The cinnamldehyde reagent referred to contains 0.15g. or p-dimethylaminocinnamaldehyde; 25 g of sodium dodecyl sulfate; 25 ml. of glacial acetic acid; 50 ml of 2-methoxyethanol and 925 ml. of distilled water.

What is claimed is:

1. A method for the rapid identification of microorganisms within about 6 hours of incubation of said microorganisms selected from the group consisting of genera and species of yeast and other fungal microorganisms comprising:
    (a) culturing an unknown yeast or other fungal microorganisms in a non-inhibitory mycological culture medium for 48 to 72 hours at 25°-30° C. to stimulate the production or multiply the presence of colonies containing one or more enzymes characteristic of said microorganism;
    (b) suspending and homogenously mixing, from the medium of step(a), a sufficient number of morphologically similar colonies of the so cultured unknown microorganism containing said enzyme(s) in an aqueous suspending medium to prepare an inoculum having a turbidity equivalent of at least McFarland No. 3 of the unknown microorganism;
    (c) separately mixing the inoculum with one or more substrates selected from a first group selected from the group consisting of chromogenic substrates for detecting the presence or absence of acetate esterase, leucyl-glycine aminopepetidase, and glycyl-glycine aminopeptidase, said chromogenic substrates capable of reacting with said enzyme(s) to produce a colored product or a product convertible to a colored product said products selected from the group consisting of β-naphthylamine, p-nitroaniline, indoxyl, o-nitrophenol, p-nitrophenol, β-naphthol and substituted naphtols and said substrates further defined as being the esters and amides formed between the group consisting of acetic acid, leucyl-glycine and glycyl-glycine with the products;
    (d) incubating the inoculum substrate mixtures of step(c) at about 36° C. from about 2 to about 6 hours to obtain the product(s) whereby the unknown yeast or other fungal microorganism is identified by comparing detected enzyme activity characteristic of said microorganism with characteristic enzyme activity of known genera and species of yeast and other fungal microorganisms.

2. The method of claim 1 in which the inoculum is also separately mixed and incubated with a substrate selected from the group consisting of p-nitrophenyl-N-acetyl-BD-galactosaminide for detecting the presence or absence of N-acetyl-BD-galactosaminidase and L-proline-p-nitroanilide for detecting L-proline aminopeptidase.

3. The method of claim 1 in which the substrates are selected from indoxyl acetate, leucyl-glycine-β-naphthylamide and glycyl-glycine-β-naphthylamide.

4. The method of claim 1 in which the substrate reactive to the enzyme acetate esterase identifies and distinguishes a species from a species pair selected from the group consisting of
B.(Tr.)capitatum/C.lambica,
B.(Tr.)capitatum/Pr.stagnora,
B.(Tr.)capitatum/Pr.zopfii,
B.(Tr.)captiatum/T.glabrata,
C.albicans/C.lusitaniae,
C.albicans/C.parapsilosis,
C.albicans/C.paratropicalis,
C.albicans/C.stellaoidea,
C.albicans/C.tropicalis
C.krusei/C.lambica,
C.krusei/Pr.zopfii,
C.krusei/T.glabrata,
C.lusitaniae/T.candida,
C.stellaoidea/Cr.terreus,
Cr.albidus/Cr.neoformans,
Cr.albidus/Cr.uniguttulatus,
Cr.neoformans/Tr.beigelii,
H.anomala/S.cerevisiae,
Th.glutinis/S.cerevisiae,
Rh.rubra/S.cerevisiae,
S.cerevisiae/Sp.salmonicolor, and
T.candida/Tr.beigelii.

5. The method of claim 1 in which the substrate reactive to the enzyme leucyl-glycine aminopeptidase identifies and distigushes a species from a species pair selected from the group consisting of
B.(Tr.)captiatum/Pr.zopfii,
C.albicans/C.paratropicalis,
C.albicans/C.tropicalis,
C.lambica/Pr.zopfii,
C.lipolytica/Pr.zopfii,
C.lusitaniae/C.tropicalis,
C.parapsilosis/C.tropicalis,
C.paratropicalis/C.stellatoidea,
C.rugosa/Geotrichum sp.,
Cr.albidus/Cr.laurentii,
Cr.albidus/Cr.neoformans,
Cr.laurentii/Tr.beigelii,
Cr.neoformans/Cr.uniguttulatus,
Cr.neoformans/Tr.beigelii, and
T.candida/Tr.beigelii.

6. The method of claim 1 in which the substrate reactive to the enzyme glycyl-glycine aminopeptidase identifies and distinguishes a species from a species pair selected from the group consisting of
B.(Tr.)capitatum/C.krusei,
C.albicans/C.paratropicalis,
B.(Tr.)capitatum/C.lambica,
C.albicans/C.stellatoidea,
C.albicans/C.tropicalis,
C.guilliermondii/T.candida,
C.krusei/C.lypolytica,
C.krusei/T.glabrata,
C.lambica/C.lipolytica, and

*C.lambica/T.glabrate.*

7. The method of claim 2 which further includes separately mixing the inoculum with each of at least three substrates selected from a second group consisting of p-nitrophenylphosphate, p-nitrophenyl-βD-fucoside, p-nitrophenyl-βD-glucoside, p-nitrophenyl-βD-glucoside and o-nitrophenyl-βD-xyloside.

8. The method of claim 2 which further includes separately mixing the inoculum with each of at least five substrates selected from a third group consisting of the β-naphthylamides of glycine, L-proline, L-tryptophan, L-hydroxyproline, L-isoleucine, L-valine, L-histidine, L-tyrosine, and the di-β-naphthylamide of L-cystine.

9. A test kit for the rapid identification of clinically significant microorganisms within about 2 to about 6 hours of incubation thereof selected from the group consisting of genera and species of yeast and other fungal micoorganisms and comprising a series of test chambers some of said chambers separately containing in dried form one each of a first group of test substrates selected from the group consisting of chromogenic substrates for detecting the presence or absence of acetate eserase, leucyl-glycine aminopeptidase and glycyl-glycine aminopeptidase, said chromogenic substrates capable of reacting with said enzyme(s) to produce a colored product or a product convertible to a colored product and said products selected from the group consisting of β-naphthylamine, p-nitroaniline, indoxyl, o-nitrophenol, p-nitrophenol, β-naphthol and substituted naphthols and said substrates further defined as being the esters and amides formed between the group consisting of acetic acid, leucyl-glycine and glycyl-glycine with the products.

10. The test kit of claim 9 further comprising a substrate selected from the group consisting of p-nitrophenyl-N-acetyl-BD-galactosaminide and L-proline-p-nitroanilide.

11. The test kit of claim 10 further comprising in separate chambers thereof one ach of at least three substrates selected from a second group consisting of p-nitrophenylphosphate, p-nitrphenyl-βD-fucoside, p-nitrophenyl-βD-glucoside, p-nitrophenyl-βD-glucoside and o-nitrophenyl-βD-xyloside.

12. The test kit of claim 11 further comprising in separate chambers thereof one each of at least five substrates selected from a third group consisting of the β-naphthylamides of glycine, L-proline, L-tryptophan, L-hydroxyproline, L-isoleucine, L-valine, L-histidine, L-tyrosine, and the di-β-naphthylamide of L-cystine.

13. The test kit of claim 12 further comprising in a separate chamber thereof a urea substrate.

* * * * *